(12) United States Patent
Goyal et al.

(10) Patent No.: US 7,367,212 B2
(45) Date of Patent: May 6, 2008

(54) ROTATIONAL AND LINEAR SHOCK APPARATUS

(75) Inventors: Suresh Goyal, Warren, NJ (US); Bryan Anthony Rodgers, Limerick (IE); Marie-Loic Leport, Toulouse (FR)

(73) Assignees: Lucent Technologies Inc., Murray Hill, NJ (US); University Of Limerick, Limerick (IE)

( * ) Notice: Subject to any disclaimer, the term of this patent is extended or adjusted under 35 U.S.C. 154(b) by 230 days.

(21) Appl. No.: 11/378,082

(22) Filed: Mar. 17, 2006

(65) Prior Publication Data

US 2007/0220949 A1    Sep. 27, 2007

(51) Int. Cl.
*G01M 7/00* (2006.01)

(52) U.S. Cl. .................................... 73/12.04
(58) Field of Classification Search ..... 73/12.01–12.04
See application file for complete search history.

(56) References Cited

U.S. PATENT DOCUMENTS

| | | | |
|---|---|---|---|
| 4,006,626 A * | 2/1977 | Ruzicka et al. ............ | 73/12.02 |
| 4,023,396 A | 5/1977 | Yakshin et al. | |
| 4,426,683 A | 1/1984 | Kissell | |
| 4,433,570 A | 2/1984 | Brown et al. | |
| 4,531,401 A * | 7/1985 | Nelson et al. ............. | 73/12.06 |
| 4,980,526 A | 12/1990 | Reneau | |
| 5,000,030 A | 3/1991 | Umeda et al. | |
| 5,355,716 A | 10/1994 | Castelli | |
| 5,450,742 A | 9/1995 | Baltz et al. | |
| 6,308,555 B1 | 10/2001 | Liem et al. | |
| 6,374,661 B1 | 4/2002 | Buratynski et al. | |
| 6,443,013 B1 | 9/2002 | Smith et al. | |

OTHER PUBLICATIONS

S. Goyal et al., "Shock Protection of Portable Electronic Products: Shock Response Spectrum, Damage Boundary Approach, and Beyond," Shock and Vibration, vol. 4, No. 3, pp. 169-191 (1997).
S. Goyal et al., "The Dynamics of Clattering I: Equation of Motion and Examples," J. of Dynamic Systems, Measurement, and Control, Mar. 1998, vol. 120, p. 83-93.
S. Goyal et al., "The Dynamics of Clattering II: Global Results and Shock Protection," J. of Dynamic Systems, Measurement, and Control, vol. 120, Mar. 1998, pp. 94-102.
S. Goyal et al., "Simulation of Dynamics of Interacting Rigid Bodies Including Friction II: Software System Design and Implementation," Engineering with Computers (1994) 10, pp. 175-195.

* cited by examiner

*Primary Examiner*—Max Noori

(57) ABSTRACT

One embodiment of a shock apparatus comprises at least one linear impact object capable of movement along a first substantially linear path; a rotational impact object capable of rotation about an axis of rotation and movement along a second substantially linear path parallel to the first substantially linear path, a mass of the linear impact object being greater than an effective mass of the rotational impact object; and a guide to guide the movement of the linear and rotational impact objects along the first and second substantially linear parallel paths. In one embodiment, the linear impact object comprises an impact portion for impacting the rotational impact object, the impact portion having a selectable position, and selecting the position determining the relative proportion of rotational and linear shock accelerations which an impact between the linear impact object and the rotational impact object provides to the rotational impact object.

21 Claims, 10 Drawing Sheets

ROTATIONAL AND LINEAR SHOCK APPARATUS

CROSS REFERENCE TO RELATED APPLICATION

This application is related to U.S. patent application Ser. No. 11/378,019, entitled "Shock Apparatus," filed concurrently with the present Application, and which is hereby incorporated by reference in its entirety.

BACKGROUND OF THE INVENTION

1. Field of the Invention

The present invention generally relates to mechanical shock, and more particularly to apparatuses and methods for providing rotational and linear mechanical shocks.

2. Description of the Related Art

Many types of devices and structures require the ability to withstand a certain level of acceleration applied over a certain time period, i.e., a shock acceleration. Examples of such devices include micro-electro-mechanical systems (MEMs), nanodevices, photonic devices, and RF devices. Some apparatuses and methods used to deliver shock accelerations include drop testing, i.e., dropping a test object from a predetermined height; and ballistic testing, i.e., attaching the test object to a ballistic projectile which is launched by a cannon. A Split Hopkinson Bar may also be used. Such apparatuses and methods have practical limitations. For example, drop testing is limited by the height from which an object may be dropped, which in turn limits the magnitude of acceleration that may be produced. Also, ballistic methods may be undesirably dangerous and expensive.

Also, many objects need to be accelerated to a certain velocity. Examples of such objects include satellites, some types of vehicles, and ammunition. Some apparatuses and methods used to accelerate objects to a velocity include, e.g., ballistic methods and attaching the test object to a rocket. One limitation of such methods is that they may be undesirably dangerous and expensive.

SUMMARY OF THE INVENTION

Various deficiencies of the prior art are addressed by the present invention, one embodiment of which is a shock apparatus. In one embodiment, the shock apparatus comprises at least one linear impact object capable of movement along a first substantially linear path; a rotational impact object capable of rotation about an axis of rotation and movement along a second substantially linear path parallel to the first substantially linear path, a mass of the linear impact object being greater than an effective mass of the rotational impact object; and a guide to guide the movement of the linear and rotational impact objects along the first and second substantially linear parallel paths. In one embodiment, the linear impact object comprises an impact portion for impacting the rotational impact object, the impact portion having a selectable position, and selecting the position determining the relative proportion of rotational and linear shock accelerations which an impact between the linear impact object and the rotational impact object provides to the rotational impact object.

In one embodiment, a method comprises providing at least one linear impact object capable of movement along a first substantially linear path and a rotational impact object capable of rotation about an axis of rotation and movement along a second substantially linear path, a mass of the linear impact object being greater than an effective mass of the rotational impact object; guiding the movement of the first impact object along the first substantially linear path and the second impact object along the second substantially linear path; and impacting the linear impact object and the rotational impact object in a plurality of temporally ordered impacts. In one embodiment, the method also comprises providing an impact portion of the linear impact object for impacting the rotational impact object, the impact portion having a selectable position; and selecting the position of the impact portion to determine the relative proportion of rotational and linear shock acceleration which an impact between the linear impact object and the rotational impact object provides to the rotational impact object.

In one embodiment, the shock apparatus comprises a first impacting means for providing at least one linear velocity changing impact involving a linear impact object, the at least one linear velocity changing impact resulting in an impacted linear impact object having a resulting linear velocity which is changed relative to an initial linear velocity of the linear impact object; and a second impacting means for providing a rotational velocity changing impact between the impacted linear impact object and a rotational impact object, the rotational velocity changing impact resulting in an impacted rotational impact object having a rotational velocity different than an initial rotational velocity of the rotational impact object. In one embodiment, the shock apparatus comprises a rotational velocity selection means for selecting the rotational velocity provided by the rotational velocity changing impact. In one embodiment, the rotational velocity selection means comprises an impact portion having selectable properties, the impact portion being of at least one of: the first impact object or the second impact object.

BRIEF DESCRIPTION OF THE DRAWINGS

So that the manner in which the above recited features of the present invention can be understood in detail, a more particular description of the invention, briefly summarized above, may be had by reference to embodiments, some of which are illustrated in the appended drawings. It is to be noted, however, that the appended drawings illustrate only typical embodiments of this invention and are therefore not to be considered limiting of its scope, for the invention may admit to other equally effective embodiments.

To facilitate understanding, identical reference numerals have been used, where possible, to designate identical elements that are common to the figures.

DETAILED DESCRIPTION

Figure 1B:
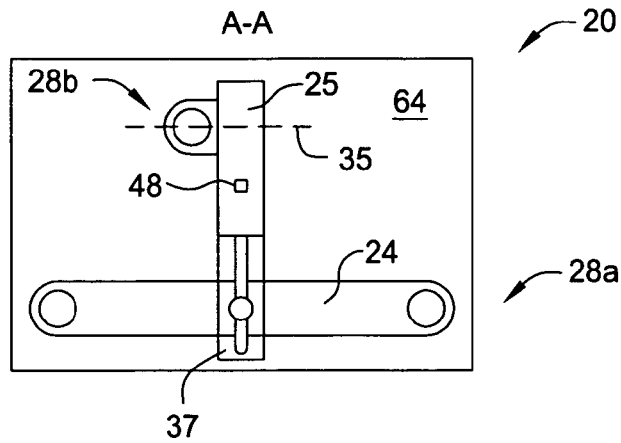
FIGS. 1a-c depict front, top sectional and side sectional views, respectively, of an embodiment of a shock apparatus according to the present invention.
Figure 1A:
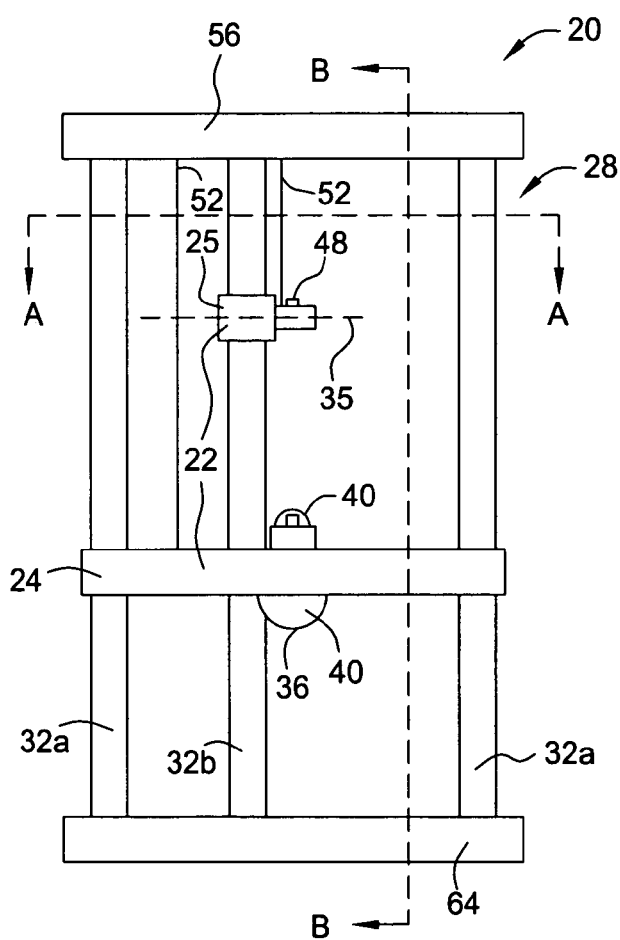
Figure 1C:
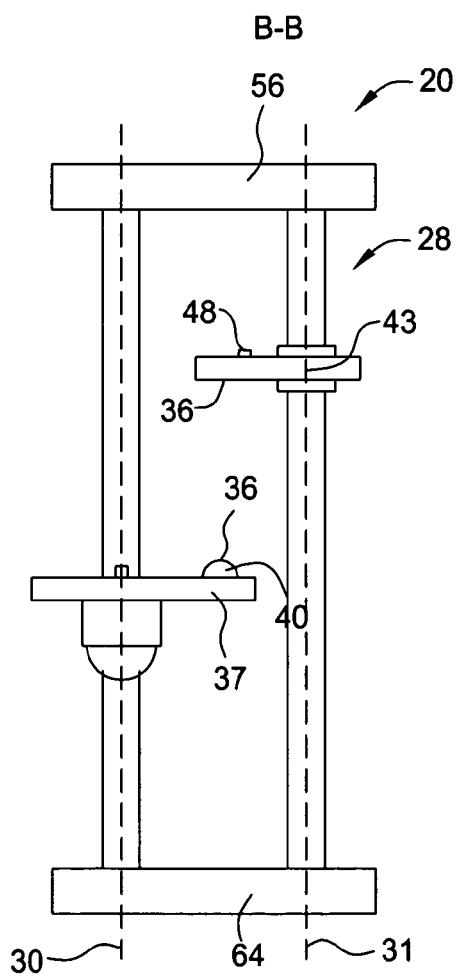

An embodiment of a shock apparatus 20 according to the present invention is depicted in FIGS. 1a-c. The shock apparatus 20 is capable of delivering a mechanical shock to a test object 48. The shock is an acceleration applied to the test object 48. Equivalently, the shock can be characterized as a change in velocity of the test object 48. The shock acceleration comprises an acceleration magnitude as a function of time, and comprises a linear translational component and a rotational component. A linear translational acceleration is a rate of change of a linear translational velocity. A rotational acceleration is a rate of change of a rotational velocity.

Figure 2A:
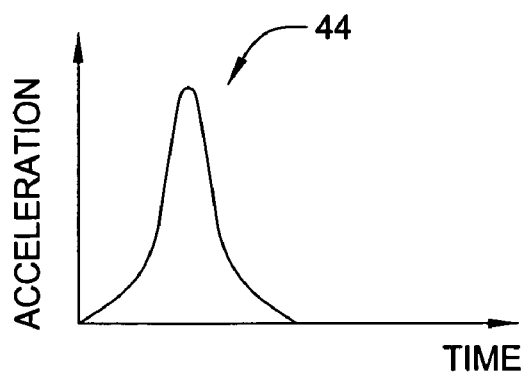
FIGS. 2a-c are graphs depicting representations of embodiments of a shock acceleration pulse delivered by an embodiment of the shock apparatus.

In one embodiment the linear component, the rotational component, or both, of the shock acceleration delivered by the shock apparatus 20 comprises a shock acceleration pulse 44. FIG. 2a depicts one embodiment of the shock acceleration pulse 44. In FIG. 2a, the x-axis represents time and the y-axis represents acceleration magnitude. The magnitude of the area under the curve representing the acceleration pulse 44 represents the change in velocity imparted by the shock acceleration pulse 44 to the test object 48. In one embodiment, the shock acceleration delivered by the shock apparatus 20 comprises an acceleration as a function of time having a form other than that of the pulse 44.

Figure 3B:
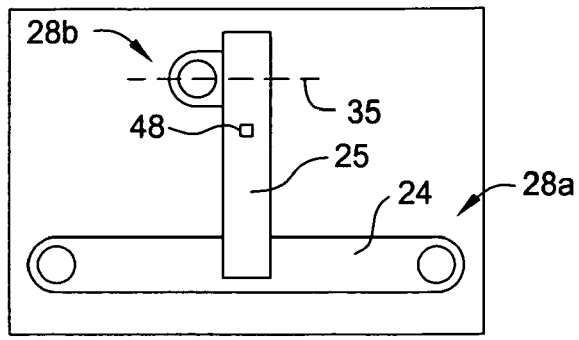
FIGS. 3a-c depict front, top sectional and side sectional views, respectively, of an embodiment of a shock apparatus having a plurality of linear impact objects.
Figure 3A:
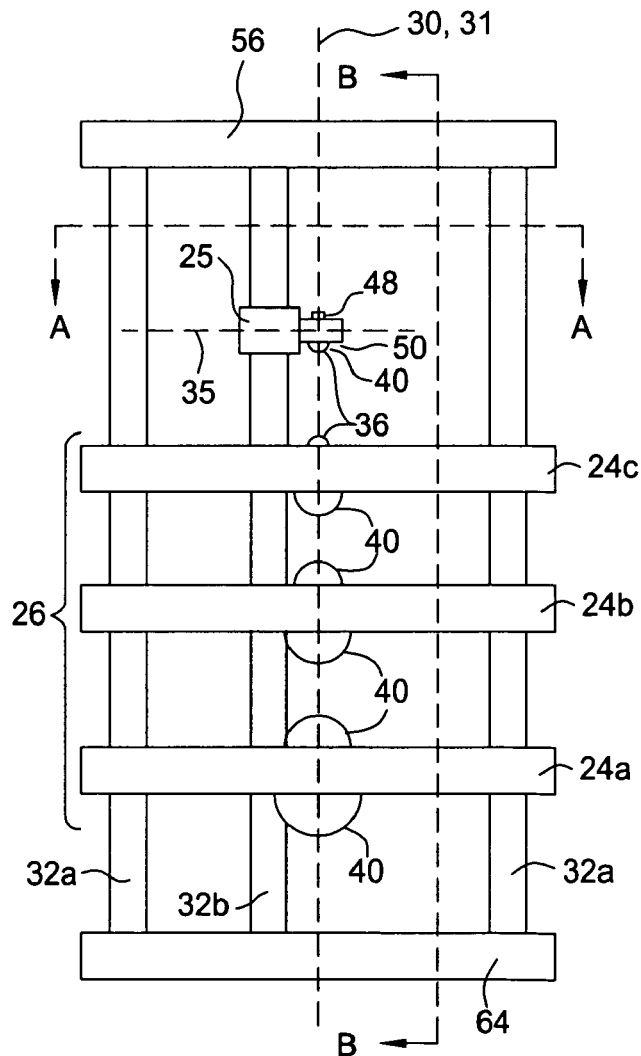
Figure 3C:
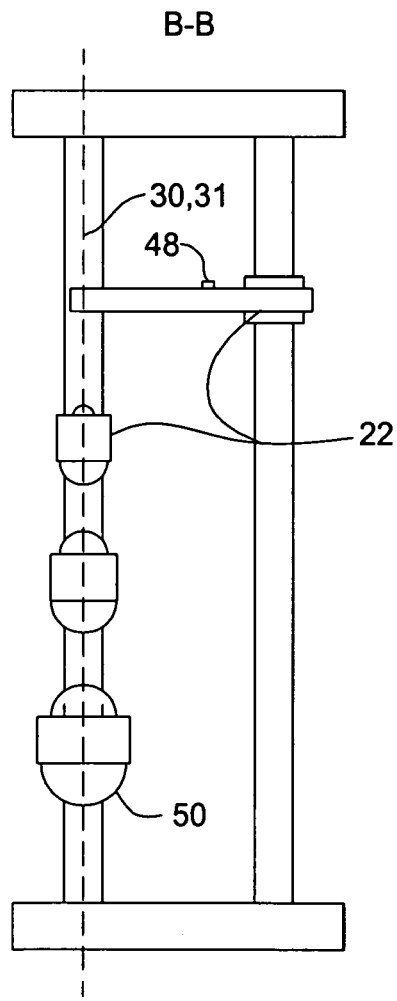

The shock apparatus 20 comprises a plurality of impact objects 22, including at least one linear impact object 24 and one rotational impact object 25. The linear impact object 24 is capable of moving along a first substantially linear path 30. In one embodiment, the shock apparatus 20 comprises a plurality of linear impact objects 24. For example, FIGS. 3a-c depict an embodiment of the shock apparatus 20 comprising three linear impact objects 24. In one embodiment, the plurality of linear impact objects 24 are arranged in a spatial order 26 along the first substantially linear path 30 of movement of the linear impact objects 24. For example, in the embodiment depicted in FIG. 3a-c, the linear impact objects 24 are arranged in the spatial order 26 along the first substantially linear path 30 with a first linear impact object 24a being first in the spatial order 26, a second linear impact object 24b being second in the spatial order 26 and a third linear impact object 24c being third in the spatial order 26.

Figure 4A:
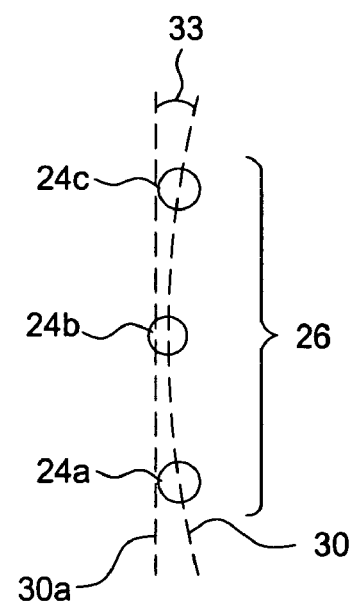
FIGS. 4a-b depict schematic views of embodiments of a substantially linear path of movement of the plurality of impact objects of an embodiment of the shock apparatus.
Figure 4B:
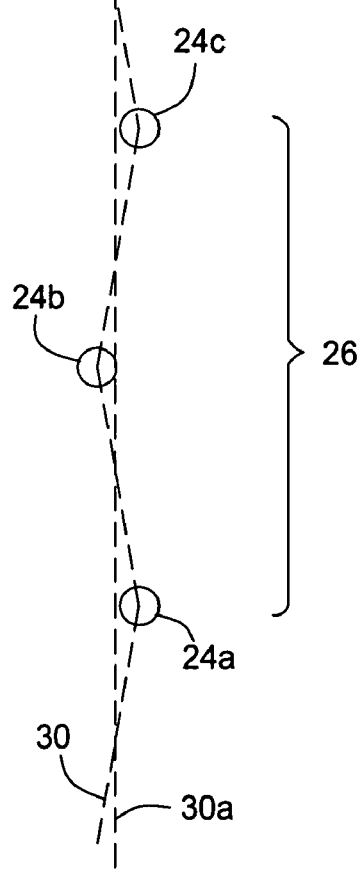

The first substantially linear path 30 may deviate from linearity by at most a predetermined amount. In one embodiment, the first substantially linear path 30 comprises a purely linear path 30a. In one embodiment, the substantially linear path 30 deviates from a purely linear path 30a as measured by an angle 33 between the substantially linear path 30 and the purely linear path 30a, the angle 33 being no greater than about 15°. For example, FIGS. 4a,b depict embodiments of the first substantially linear path 30 which deviate from the purely linear path 30a by the angle 33 no greater than about 15°. Specifically, FIG. 4a depicts an embodiment of the path having curvature which falls within the predetermined angular deviation, and FIG. 4b depicts an embodiment of the path 30 having points offset from the purely linear path 30a such that the path 30 connecting the points falls within the predetermined angular deviation.

In one embodiment, the spatial order 26 is an ordering of the linear impact objects 24 according to decreasing value of mass of each of the linear impact objects 24. For example, in the embodiment depicted in FIG. 3a, the first linear impact object 24a is first in the spatial order 26 and has a first mass, the second linear impact object 24b is second in the spatial order and has a second mass less than the first mass, the third linear impact object 24c is third in the spatial order and has a third mass less than the second mass.

The plurality of impact objects 22 of the shock apparatus 20 comprises a rotational impact object 25. The rotational impact object 25 is capable of translational movement along a second substantially linear path 31. The rotational impact object 25 is also capable of rotation about an axis of rotation 35. The axis of rotation 35 is fixed relative to a part of the rotational impact object 25 and moves with the rotational impact object 25 as it moves along the second substantially linear path 31. In the same manner as the first substantially linear path 30, in one embodiment the second substantially linear path 31 comprises a purely linear path, and in one embodiment the second substantially linear path 31 deviates from a purely linear path by a predetermined amount. In one embodiment, the second substantially linear path 31 deviates from a purely linear path by at most the same amount as described above for the first substantially linear path 30.

Each of the plurality of impact objects 22 comprises at least one impact portion 36 which is the portion 36 of the impact object 22 where an impact with another impact object 22 or another object 64, such as for example a fixed-position object, takes place.

The rotational impact object 25 has an effective mass, $m_{eff}$, which may differ from the mass of the rotational impact object 25 depeding upon the configuration of the shock apparatus 20. Generally speaking, the effective mass of the rotational impact object 25, in the context of the rotational impact object 25 being involved in an impact in which the impact portion 36 of the rotational impact object 25 is located at a particular location of the rotational impact object 25, is the point mass that would experience the same motion as the particular location of the impact portion 36 on the rotational impact object 25 when subjected to identical forces as the impact applies to the impact portion 36 of the rotational impact object 25. Besides the particular location of the impact portion 36, the effective mass also depends on the direction of the applied force. A detailed description of the derivation of the effective mass for a general object is in the Appendix A of "Simulation of Dynamics of Interacting Rigid Bodies Including Friction II: Software System design and Implementation," by Goyal, S., Pinson, E., and Sinden, F., Engineering with Computers, Vol. 10, pp. 175-195, 1994.

In one embodiment, the rotational impact 25 object comprises a rod. For a rod of length 2L, the effective mass for an impact at the end of the rod, which applies a force in a direction perpendicular to the rod, is given by $m_{eff}=M/(1+L^2/\rho_g^2)$, where M is the mass of the rod and $\rho_g$ is the radius of gyration of the rod. For a uniform rod this implies that the effective mass for an impact at the end of the rod is $m_{eff}=M/4$.

In one embodiment, the effective mass of the rotational impact object 25 is less than the mass of any of the linear impact objects 24. In another embodiment, the mass of the rotational impact object 25 is less than the mass of any of the linear impact objects 24. Because the effective mass of the rotational impact object 25 is always less than the mass of the rotational impact object 25, an embodiment in which the mass of the rotational impact object 25 is less than the mass of any of the linear impact objects 24 is also an embodiment in which the effective mass of the rotational impact object 25 is less than the mass of any of the linear impact objects 24.

In one embodiment, the test object 48 is attached to the rotational impact object 25. The test object 48 experiences the shock acceleration experienced by the rotational impact object 25 at the attachment location. The location of attachment of the test object 48 to the rotational impact object 25 can be varied. Varying the location of attachment of the test object 48 to the rotational impact object 25 can be used to select the relative proportions of the rotational and linear shock components experienced by the test object 48.

The shock apparatus 20 comprises a guide 28 to guide the movement of the plurality of impact objects 22 along the first and second substantially linear paths 30, 31. In one embodiment, the guide 28 comprises first and second separate guide portions 28a, 28b to guide the movement of the linear and rotational impact objects 24, 25, respectively. However, in one embodiment, the same guide elements that guide the linear impact objects 24 also guide the rotational impact object 25. In one embodiment, the first and second substantially linear paths 30, 31 coincide or partially coincide. In one embodiment, the first and second substantially linear paths 30, 31 are parallel. The guide 28 is capable of maintaining the spatial order 26 of the plurality of linear impact objects 24 during at least a portion of a plurality of impacts experienced by the plurality impact objects 24 during operation of the shock apparatus 20. The impact objects 22 and the guide 28 are arranged such that linear impact objects 24 which are adjacent to each other in the spatial order 26 are capable of impacting each other as they move along the first path 30, and that at least one linear impact object 24 is capable of impacting the rotational impact object 25 as the at least one linear impact object 24 moves along the first path 30 and the rotational impact object 25 moves along the second path 31.

For example, in the embodiment depicted in FIGS. 1a-c, the linear impact object 24 is capable of moving along the first path 30 to impact both the other object 64 (which can be a fixed position object or a variable position object) and the rotational impact object 25, and the rotational impact object 25 is capable of moving along the second path 31 to impact the linear impact object 24. In the embodiment depicted in FIGS. 3a-c, the first linear impact object 24a is capable of moving along the first path 30 to impact both the other object 64 and the second linear impact object 24b, the second linear impact object 24b is capable of moving along the first path 30 to impact both the first linear impact object 24a and the third linear impact object 24c, the third linear impact object 24c is capable of moving along the first path 30 to impact both the second linear impact object 24b and the rotational impact object 25, and the rotational impact object 25 is capable of moving along the second path 31 to impact at least the third linear impact object 24c.

Generally speaking, the guide 28 may take a variety of forms. For example, in the embodiment depicted in FIGS. 1a-c, the guide 28 comprises a first guide portion 28a comprising two guide rods 32a arranged about the associated first path 30 and a second guide portion 28b comprising a guide rod 32b arranged about the second path 31.

Figure 5A:
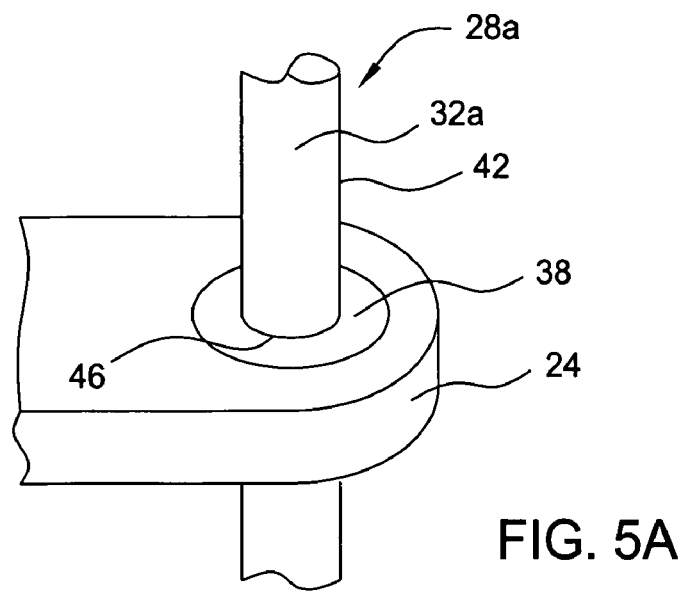
FIGS. 5a-b depict partial perspective views of embodiments of an interface between the guide and the linear impact object, in FIG. 5a, and between the guide and the rotational impact object, in FIG. 5b.

The impact object 22 comprises a means to move along the guide 28. In one embodiment, the guide 28 comprises a surface 42 which contacts a surface 46 of the impact object 24. In one embodiment, the impact object 22 comprises a means to slide along the surface 42 of the guide 28. For example, in the embodiment depicted in FIGS. 1a-c, the linear impact objects 24 each comprise at least one linear bearing 38 that enables the linear impact objects 24 to slide along the guide rods 32a with a minimum of frictional resistance. FIG. 5a depicts a partial perspective view of an embodiment of the connection between the linear impact object 24 and the first guide portion 28a. FIG. 5a depicts the contacting surfaces 42, 26 of the guide 28 and the linear impact object 24, and the linear bearing 38. The linear bearing 38 has a circular opening sized to accommodate the diameter of the guide rod 32a.

Figure 5B:
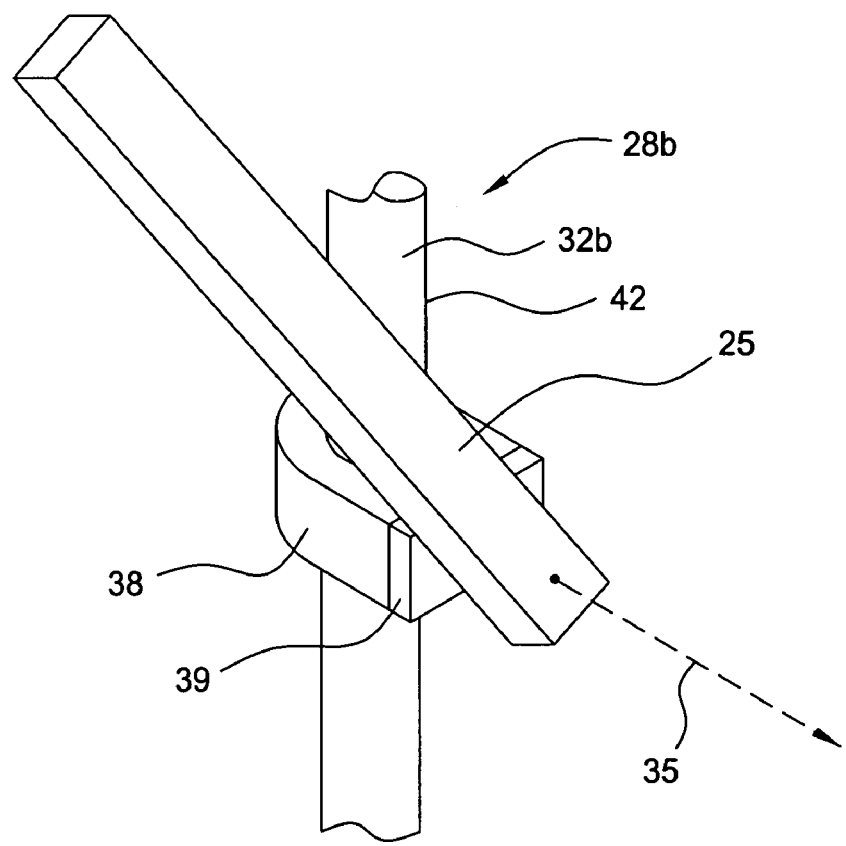

The rotational impact object 25 comprises both a means to move along the guide 28 and a means to rotate about the rotational axis 35. As discussed in the previous paragraph, in one embodiment, the rotational impact object 25 comprises a means to slide along the surface 42 of the guide 28, including in one embodiment comprising the linear bearing 38. The means to rotate about the rotational impact object 25 determines the location of the axis of rotation 35 relative to the rotational impact object 25. In one embodiment, the means to rotate about the rotational axis 35 comprises a rotational bearing 39 that enables the rotational impact object 25 to rotate about the axis of rotation 35 with a minimum of frictional resistance. FIG. 5b depicts a partial perspective view of an embodiment of the connection between the rotational impact object 25 and the second guide portion 28b. FIG. 5b depicts the contacting surfaces 42, 46 of the guide 28 and the rotational impact object 25, and the linear and rotational bearings 38, 39. The linear bearing 38 has a circular opening sized to accommodate the diameter of the guide rod 32b. In one embodiment, the linear and rotational bearings 38, 39 are combined into a single bearing.

Variation of the shape, size and weight of each of the plurality of impact objects 22 is possible. Each of the plurality of impact objects 22 comprises at least one impact portion 36 which is the portion 36 of the impact object 22 where an impact with another impact object 22 or another object 64, such as for example a fixed-position object, takes place. In one embodiment, the plurality of impact objects 22 comprise a specific impact object 22 having a shape, size, structure and material different from another specific impact object 22.

In one embodiment, the rotational impact object 24 has a center of percussion 43 located relative to the impact portion 36 of the rotational impact object 25. The impact portion 36 of the rotational impact object 25 is where the rotational impact object 25 impacts the linear impact object 24. The center of percussion 43 is the part of the rotational impact object 25 which experiences purely rotational acceleration when the rotational impact object 25 experiences a linear impact at the so-called sweet spot of the rotational impact object 25. In one embodiment, the center of percussion 43 of the rotational impact object 25 coincides with the axis of rotation 35 of the rotational impact object, and the impact portion 36 of the rotational impact object 25 is located at the sweet spot; and this embodiment is useful for providing a purely rotational shock acceleration by the shock apparatus 20 to a test object 48 attached to the rotational impact object 25 at the center of percussion 43. In another embodiment, the center of percussion 43 of the rotational impact object 25 does not coincide with the axis of rotation 35, or the impact portion 36 is not located at the sweet spot relative to the center of percussion 43, or both, and this embodiment is useful for providing a shock acceleration by the shock apparatus 20 to the rotational impact object 25, and thus also to the test object 48, which has both linear and rotational shock acceleration components.

In one embodiment, the position of the impact portion 36 of the linear impact object 24 is adjustable. For example, FIGS. 1a-c depict one embodiment of the linear impact object 24 having an adjustable lever 37 which may adjust the position of the impact portion 36 of the linear impact object 24 relative to the rotational impact object 25. By adjusting the position of the impact portion 36 of the linear impact object 24, the impact portion 36 of the rotational impact object 25 is also adjusted, and the relative amounts of linear and rotational shock accelerations provided to the rotational impact object 25 can be controlled. In another embodiment, the position of the impact portion 36 of the rotational impact object 25 is adjusted, or the position of the axis of rotation 35 relative to the rotational impact object 25 is adjusted, or both. In one embodiment, the rotational impact object 25 comprises an adjustable position lever 37 similar to the one shown in FIGS. 1a-c. In one embodiment, the means to adjust the position of the impact portion 36 comprises a means other than an adjustable lever.

In one embodiment, the moment of inertia of the rotational impact object 25 can be selected to determine the relative proportions of rotational and linear shock applied to the rotational impact object 25 by the shock apparatus 20. The moment of inertia of an object is a measure of its mass distribution and also represents the resistance that the object offers to an applied torque. The moment of inertia can be calculated about any axis for the object. The moment of inertia is a tensor. In general, it is represented by its value in the principal axis system for the object which can then be used to calculate the moment of inertia around any other axis. For example, the moment of inertia, J, for a uniform rod about a perpendicular axis passing through the center of the rod, is given by $J=ML^2/3$, where M is the mass of the rod, and 2L is the length of the rod. The moment of inertia is also defined by $J=M\rho_g^2$. For the case of the uniform rod, $\rho_g^2=L^2/3$.

In one embodiment, the interface between the guide 28 and the rotational impact object 25 comprises a means to stop the rotation of the rotational impact object 25 at a predetermined position. In one embodiment, at least one of the rotational impact object 25 or the guide 28 comprises a latch 41 to stop the rotation of the rotational impact object 25. Stopping the rotation of the rotational impact object 25 can be useful to, e.g., prevent the rotational impact object 25 from undesirably impacting portions of the guide 28 during its rotation.

Figure 6A:
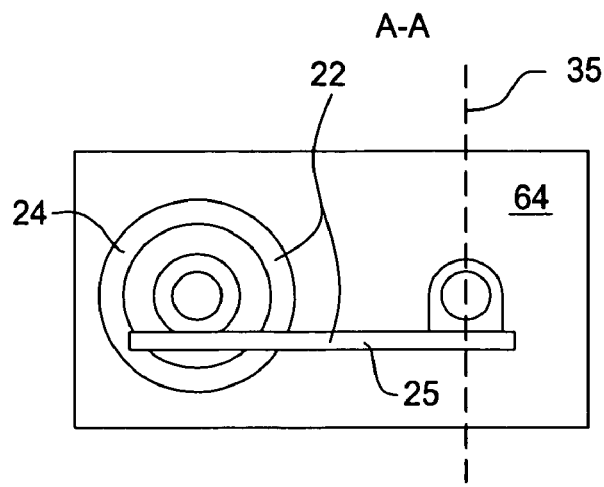
FIG. 6a-b depict a side and top sectional views, respectively, of an embodiment of the shock apparatus having only two guide rods.
Figure 6B:
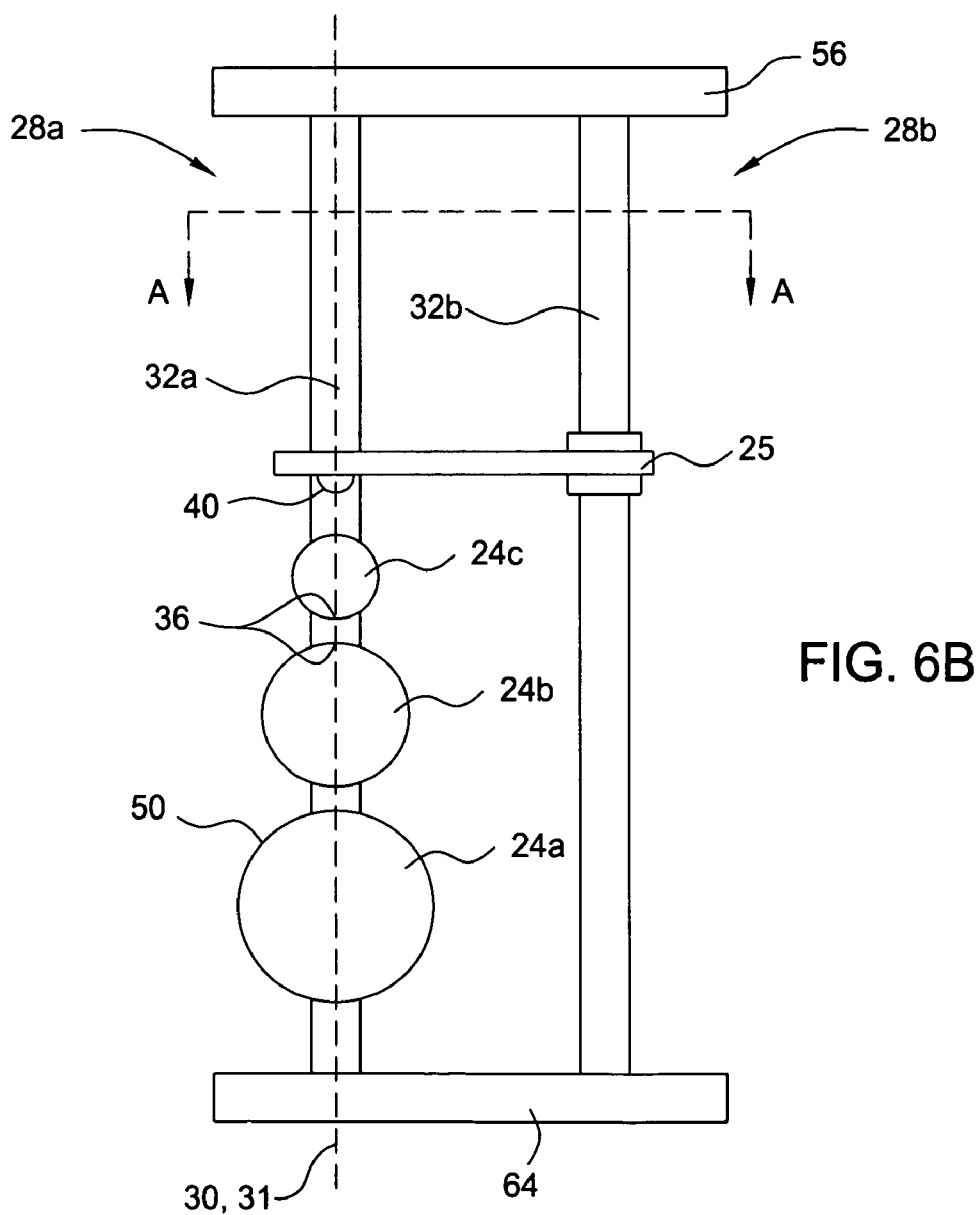

In other embodiments, the guide 28 comprises other forms. For example, FIG. 6a-b depict an embodiment of the shock apparatus 20 in which the first guide portion 28a comprises a single guide rod 32. In another embodiment, at least a portion of the guide 28 comprises an enclosing structure such as, e.g., a hollow cylinder. The guide 28 may also comprise an electromagnetic field, or other potential field, which interacts with the impact objects 22 to guide them.

A method of using the shock apparatus 20 includes a plurality of impacts occurring in a temporal order. Each of the plurality of impacts comprises at least one of: an impact between at least two linear impact objects 24, an impact between at least one linear impact object 24 and the other object 64 such as the fixed position object or a non-fixed position object, or an impact between at least one linear impact object 24 and the rotational impact object 25. Each impact is characterized by a coefficient of restitution e, which is a measure of the conservation of kinetic energy of the impact. For example, a completely elastic impact, with e=1, has 100% restitution and completely conserves the kinetic energy of the involved objects. A completely inelastic impact, with e=0, has 0% restitution and does not conserve the kinetic energy of the involved objects. In one embodiment of the shock apparatus 20, it is desirable to have relatively high restitution impacts in order to efficiently utilize the kinetic energy of the plurality of impact objects 22 and achieve the highest possible shock acceleration delivered to the test object 48.

Figure 2B:
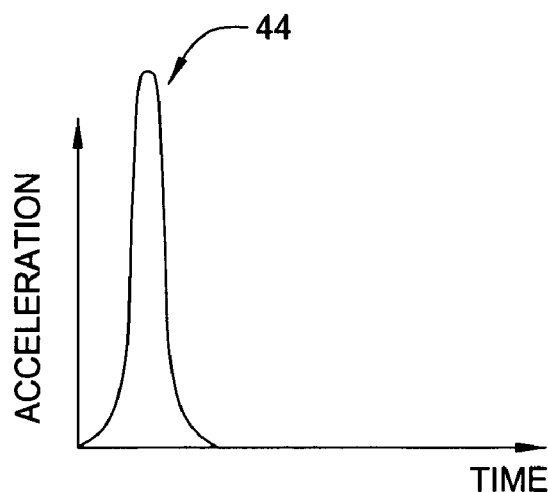
Figure 2C:
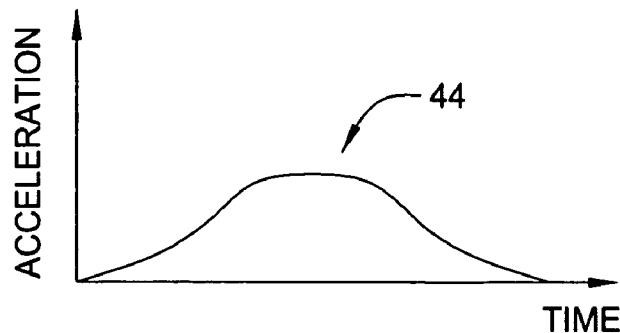

In one embodiment, the properties of the shock acceleration produced by each impact are determined by selecting the material and structural properties of the impact objects 22 involved in the impact and the impact portions 36 thereof. For example, in one embodiment, the properties of the impact portion 36 are selected to shape the shock acceleration pulse 44. In the embodiment of the shock acceleration pulse 44 depicted in FIG. 2a, the pulse 44 has a representative height and width. FIG. 2b depicts another embodiment of the shock acceleration pulse 44 in which, while maintaining the same area under the pulse 44, the height may be increased and the width decreased, i.e., the peak acceleration magnitude increased and the duration of the pulse 44 decreased. FIG. 2c depicts another embodiment of the shock acceleration pulse 44 in which, while maintaining the same area under the pulse 44, the height may be decreased and the width increased, i.e., the peak acceleration magnitude decreased and the duration of the pulse 44 increased.

In one embodiment, to provide an impact having a relatively increased acceleration magnitude, at least one of the material or structure of the impact portion 36 is selected to provide an elastic response having a relatively short time constant which enables the impact to produce a shock acceleration having a relatively higher magnitude and shorter duration. Examples of materials that are suitable for producing these relatively short time constant elastic impacts include impact portions 36 comprising relatively harder elastic materials such as, for example, metals, hard plastics, quartz, diamonds, etc. In one embodiment, it is desirable for the impact involving the test object 48, i.e., the impact involving the rotational impact object 25, to experience acceleration as high in magnitude as possible. Thus, in one embodiment, the materials and structures described in this paragraph are used especially for the impact portions 36 involved in this impact.

In one embodiment, to provide an impact having a relatively decreased acceleration magnitude, at least one of the material or structure of the impact portion 36 is selected to provide an elastic response having a relatively longer time constant which enables the impact to produce a shock acceleration having a relatively lower magnitude and longer duration. Examples of materials that are suitable for producing these relatively longer time constant elastic impacts include impact portions 36 comprising relatively softer elastic materials such as, for example, elastomers, foams, rubber, etc. In one embodiment, it is not necessary for the impacts not involving the test object 48, i.e. not involving the rotational impact object 25 to which the test object 48 is attached, to experience accelerations as high in magnitude as possible, and thus the emphasis can instead be placed on achieving as high a restitution as possible. Thus, in one embodiment, the materials and structures described in this paragraph are used for the impact portions 36 not involved in the impact involving the rotational impact object 25.

In one embodiment, the impact portion 36 comprises a protrusion 40 from the impact object 22. FIG. 1a-c depicts an embodiment of the shock apparatus 20 in which at least one of the plurality of impact objects 22 have at least one protrusion 40. In one embodiment, the selecting of the material and structural properties of the impact portion 36 to determine the properties of the shock acceleration produced by the impact includes selecting the material and structural properties of the protrusion 40. In one embodiment, the protrusion 40 has material and structural properties which are different from another part of the impact object 22.

Figure 10:
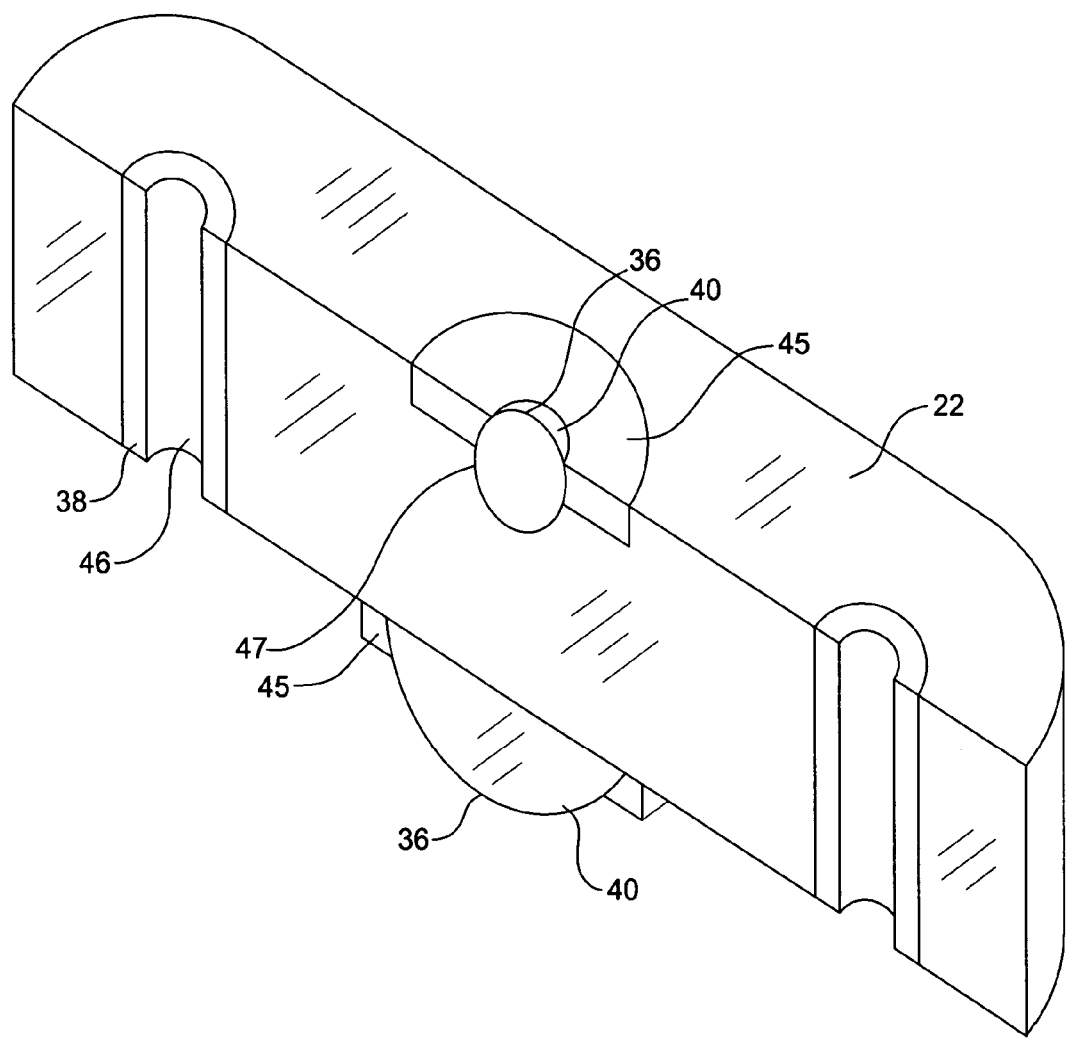
FIG. 10 depicts an embodiment of the impact object comprising an embodiment of interchangeable hemispherical protrusions.

In the embodiment depicted in FIGS. 1a-c, the impact objects 22 each in part comprise a plate. Also, in the embodiment depicted in FIGS. 3a-c, each of the impact objects 22 has an impact portion 36 comprising at least part of a hemispherical protrusion 40 from the plate. The size, thickness and material of the plates are selected to provide the predetermined mass for each of the impact objects 22. In one embodiment, the plates and the hemispherical protrusions 40 are constructed such that different hemispherical protrusions 40 are interchangeable in a given plate to allow a user to vary the shock acceleration properties of an impact, and determine the overall operating characteristics of the shock apparatus 20. For example, FIG. 10 depicts an embodiment of the impact object 22 having interchangeable hemispherical protrusions 40 secured to the impact object 22 by appropriately sized attaching plates 45. Optionally, the impact object 22 can include a recess 47 to accommodate at least a portion of the protrusion 40.

In one embodiment, one linear impact object 24 may be fixedly attached to the guide 28. For example, FIG. 9, which is discussed in more detail below, depicts an embodiment of the shock apparatus in which the first linear impact object 24a is fixedly attached to the guide 28. Thus, in this embodiment, the mass of the first linear impact object 24a comprises the mass of the guide 28.

In the embodiment depicted in FIGS. 1a-c, the guide 28 also comprises an end stop 56, e.g., a top or end plate 56, which constrains the movement of the plurality of impact objects 22 from leaving the guide 28 and the paths 30, 31 associated therewith. That is, the end stop 56 constrains the plurality of impact objects 22 to movement along a predetermined length of the paths 30, 31.

In one embodiment, at least some of the impact portions 36 of the plurality of impact objects 22 comprise a curved surface 50. In one embodiment, the impact portion 36 comprising the curved surface 50 provides desirable propagation characteristics of the shock acceleration through the impact object 22 and also shapes the shock acceleration pulse 44 as discussed above. For example, in one embodiment an impact portion 36 comprising the curved surface 50 is used to increase the restitution of an impact.

In one embodiment, the shock apparatus 20 comprises at least one spacer 52 to separate a pair of adjacent linear impact objects 24, a linear impact object 24 and the rotational impact object 25, or both, until a predetermined time during the use of the shock apparatus 20. In one embodiment, the shock apparatus 20 comprises at least one spacer 52 to correctly position an impact object 22. In one embodiment, the shock apparatus 20 comprises a plurality of spacers 52. The plurality of spacers 52 acts to separate the plurality of impact objects 22 in order to maintain the desired temporal order of impacts among the plurality of impact objects 22.

The spacer 52 may comprise any suitable apparatus or means to create the desired predetermined distance between impact objects 22 or positioning of impact objects 22. For example, in one embodiment the spacer 52 comprises a material or structure attached to the top plate 56 which in turn passes through each impact object 22 as it travels downward. In one embodiment, the shock apparatus 20 comprises a plurality of spacers 52 suspending the impact objects 22 from the top plate 56. For example, in the embodiment depicted in FIGS. 1a-c, the shock apparatus comprises two spacers 52, one of which suspends the linear impact object 24, the other of which suspends the rotational impact object 25. In one embodiment, the spacer 52 has an obstruction after it passes through each impact object 22, thereby suspending each of the impact objects 22 at a predetermined distance from the top plate 56 and the impact object 22 above it. In one embodiment, the spacer material or structure may comprise, for example, a string.

In one embodiment, the spacer 52 comprises at least one retractable arm which holds the impact object 22 in an initial position and then retracts to release the impact object 22, which then may move towards an impact.

In one embodiment, the spacer 52 comprises a spring or other compressible object. The compression characteristics, e.g., the spring constant, of the spring are selected such that it maintains suitable separation between impact objects 22 or positioning of an impact object 22 in a first scenario, e.g., at rest or traveling at a first velocity, and compresses in a second scenario, e.g., under a second set of velocities or the presence of an acceleration differential, thus allowing the impact objects 22 to impact each other at the appropriate moments.

In one embodiment, the shock apparatus 20 comprises a means to hold the rotational impact object 25 in at a predetermined rotational position, e.g. at a predetermined fixed angle relative to the guide, until an impact with the linear impact object 24.

In one embodiment, instead of a separate spacer 52, the impact object 22 comprises an integral structure or portion which achieves a similar function. For example, in one embodiment, the impact object 22 comprises a compressible portion of the impact object 22 which maintains a separation distance between less compressible portions of the impact objects 22, other portions of the impact objects 22, or both. In such an embodiment, there is no need for a spacer 52 which is a separate object from the impact object 22. Instead, the compressible portion provides a similar function by separating the less compressible or other portions prior to the impact. For example, FIG. 9, which is discussed in more detail below, depicts an embodiment of the shock apparatus 20 comprising impact objects 22 having protrusions 40 but not separate spacers 52.

The operation of the shock apparatus 20 can be understood in part by examining linear impacts in greater detail, including examining the effect of varying the relative masses of the linear impact objects 24 involved, and also examining the effect of having a plurality of temporally ordered linear impacts. The understanding gained by examining linear impacts in greater detail is also applicable to understanding the operation of the shock apparatus in regards to impacts involving the rotational impact object 25. In one embodiment, an impact involving the rotational impact object 25 translates the characteristics of a linear impact, e.g. the linear component of shock acceleration, to a rotational context, e.g. the rotational component of shock acceleration. In one embodiment, an impact involving the rotational impact object 25 translates the characteristics of a linear impact, e.g. the linear component of shock acceleration, to both a linear and a rotational context, e.g. both the linear and rotational component of shock acceleration.

FIGS. 7a-e depict moments in time of various scenarios before and after a linear impact between two linear impact objects 24 in which the ratio of the masses of the linear impact objects 24 is varied across the scenarios. The scenarios depicted in FIGS. 7a-e assume that impacts realize 100% restitution and are also depicted horizontally, thus removing the effect of gravity. The understanding gained by examining the scenarios depicted in FIGS. 7a-e is believed to be nonetheless relevant to relatively high, yet non-100%, restitution impacts, and also to embodiments of the shock apparatus 20 positioned vertically, e.g., as depicted in FIGS. 1a-c, as gravitational acceleration typically has a relatively small magnitude in comparison to other accelerations produced by the shock apparatus 20.

Figure 7A:
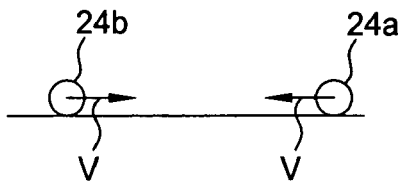
FIGS. 7a-e depict embodiments of various moments in time before and after an impact between two impact objects.

FIG. 7a depicts an initial moment in time in which two linear impact objects 24 are traveling towards each other before an impact. The first and second linear impact objects 24a,b each have a velocity of magnitude V, but in opposite directions. FIG. 7b-e depict different scenarios of a moment in time after an impact between the first and second linear impact objects 24a,b in which the ratio of the masses of the linear impact objects 24a,b is varied.

Figure 7B:
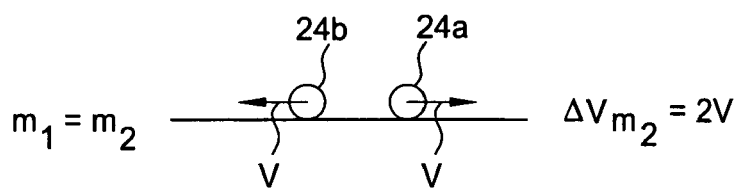

FIG. 7b depicts a scenario in which the first mass, m1, of the first linear impact object 24a and the second mass, m2, of the second linear impact object 24b, are equal, i.e., m1=m2. In this scenario, after the impact both linear impact objects 24a,b travel away from each other in opposite directions, each having a new velocity having magnitude V equal to the initial velocity magnitude but in the opposite direction relative to the initial velocity directions. Thus, in this scenario, both linear impact objects 24a,b experience a change in velocity ΔV in which ΔV=2V.

Figure 7C:
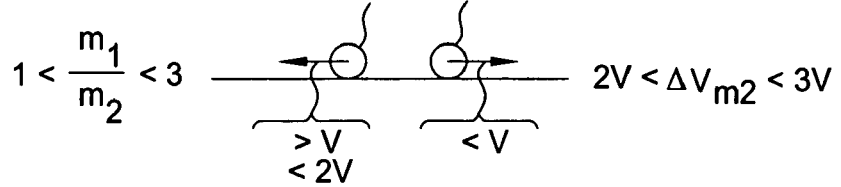

FIG. 7c depicts a scenario in which 1<m1/m2<3. In this scenario, after the impact, the second linear impact object 24b travels away from the first linear impact object 24a at a velocity V2 in the opposite direction from its initial velocity and having a value in which V<V2<2V. The first linear impact object 24a travels away from the second linear impact object 24b at a velocity V1 in which V1<V in a direction opposite to its initial velocity. Thus, in this scenario the second linear impact object 24b experiences a change in velocity ΔVm2 in which 2V<ΔVm2<3V.

Figure 7D:
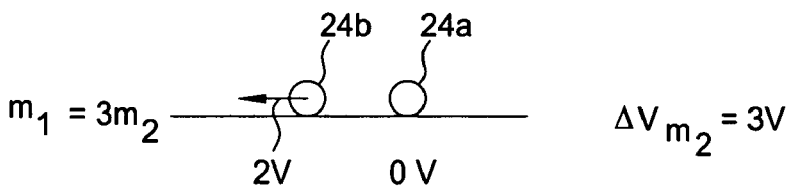

FIG. 7d depicts a scenario in which m1=3m2. In this scenario, after the impact, the second linear impact object 24b travels away from the first linear impact object 24a at a velocity V2 in the opposite direction from its initial velocity and having a magnitude in which V2=2V. The first linear impact object 24a comes to a rest after the impact. Thus, in this scenario the second linear impact object 24b experiences a change in velocity ΔVm2 in which ΔVm2=3V.

Figure 7E:
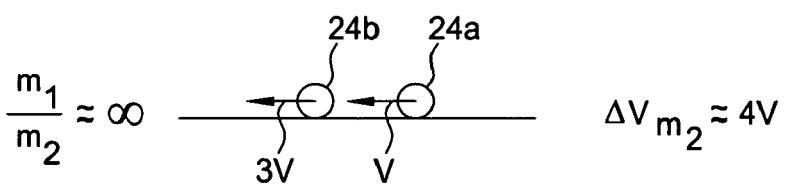

FIG. 7e depicts a scenario in which m1/m2≈∞. In this scenario, after the impact both linear impact objects 24a,b move towards the left in FIG. 6e, with the second linear impact object 24b traveling at a velocity V2≈3V in a opposite direction from the direction of its initial velocity. The first linear impact object 24a will travel at approximately the same velocity V in the same direction as the direction of its initial velocity. Thus, in this scenario, the second linear impact object 24b experiences change in velocity ΔVm2 in which ΔVm2≈4V.

From the scenarios depicted in FIGS. 7a-e, it can be understood that a special regime of velocity acceleration of the second linear impact object 24b exists which efficiently utilizes the momentum of the first linear impact object 24a. Particularly, in the embodiments in which the first mass has a value which is at least 3 times the value of the second mass, the first linear impact object 24a is not turned back. This indicates a special regime of velocity acceleration. Thus, in one embodiment of the shock apparatus 20, the ratio of masses of adjacent linear impact objects 24 in the spatial order 26 is greater than or equal to 3. For example, in one embodiment having a plurality of linear impact objects 24, the ratios of the masses of adjacent linear impact objects 24 have values in which m1/m2>3, m2/m3≧3, m3/m4≧3, etc., wherein m3 is the mass of the third linear impact object 24c, m4 is the mass of the fourth linear impact object 24d, etc. However, although the regime in which m1/m2≧3 marks a special regime of operation of the shock apparatus 20, velocity acceleration nonetheless still occurs for m1>m2, and thus in one embodiment, as discussed above, the masses have values according to m1>m2, m2>m3, m3>m4, etc.

The special regime of velocity acceleration is also relevant to the impact involving the rotational impact object 25, and thus in one embodiment, the mass of the linear impact object 24 involved in the impact with the rotational impact object 25 is at least three times greater than the effective mass of the rotational impact object 25.

Figure 8A:
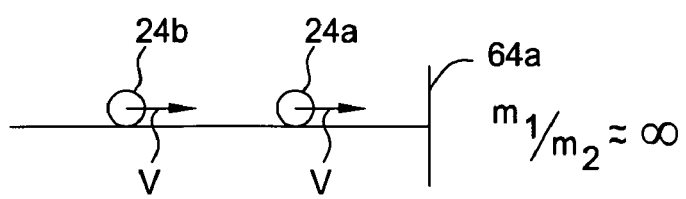
FIGS. 8a-c depict embodiments of various moments in time before and after a plurality of impacts involving a first and second impact object and a fixed-position object.
Figure 8B:
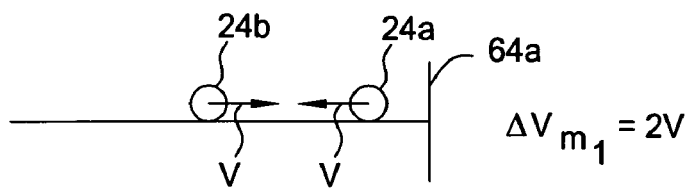
Figure 8C:
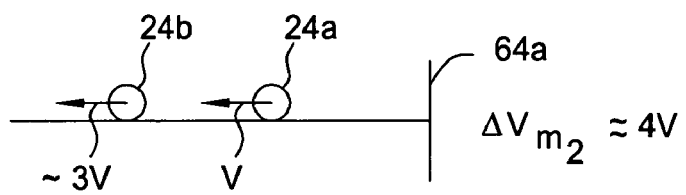

The operation of the shock apparatus 20 can be further understood by examining the cumulative velocity acceleration of a plurality of linear impacts between linear impact objects 24. FIGS. 8a-c depict an embodiment of various moments in time of an impact scenario between two linear impact objects 24 and the other object 64, which in the depicted scenario is the fixed position object 64a. In the scenarios depicted in FIGS. 8a-c, it is assumed that impacts realize 100% restitution and that the ratio of the mass of the first linear impact object 24a to the mass of the second linear impact object 24b is infinite, i.e., m1/m2≈∞. The understanding gained by examining the scenarios depicted in FIGS. 8a-c is believed to be nonetheless relevant to impacts having relatively high yet non-100% restitution and impacts between linear impact objects 24 having non-infinite mass ratios.

FIG. 8a depicts an embodiment of an initial moment in time in which two linear impact objects 24 are moving towards the fixed position object 64a, e.g., a wall. In the moment of time depicted by FIG. 8a, both linear impact objects 24 have a velocity having the same magnitude V in the same direction towards the fixed position object 64a.

FIG. 8b depicts a moment in time after the first linear impact object 24a impacts the fixed-position object 64a. In the moment in time depicted by FIG. 8b, the first linear impact object 24a has reversed its direction, while retaining the same velocity magnitude V, but moving in the opposite direction relative to its initial direction. The second linear impact object 24b is moving towards the first linear impact object 24a, which is now moving towards the second linear impact object 24b, and they both have the same velocity magnitude V, although in different directions. The moment in time depicted by FIG. 8b is before the first linear impact object 24a impacts the second linear impact object 24b.

FIG. 8c depicts moment in time after the second linear impact object 24b impacts the first linear impact object 24a. After the impact between the first and second linear impact objects 24a,b, the second linear impact object 24b has a velocity magnitude ≈3V in a direction opposite to its initial direction. The first linear impact object 24a has roughly the same velocity in the same direction as it does in FIG. 8b, due to its roughly infinite mass. The degree to which the first linear impact object 24a retains its original velocity magnitude V is related to the degree to which the mass ratio of the first mass to the second mass is infinite. As the mass ratio becomes more finite, the first linear impact object 24a loses some of its initial velocity magnitude after the impact with the second linear impact object 24b.

The depictions of FIGS. 8a-c demonstrate velocity acceleration achieved by impact objects 24 in embodiments of the shock apparatus 20. The first linear impact object 24a experiences, as a result of the impact between the first linear impact object 24a and the fixed-position object 64a, a change of velocity $\Delta Vm1$ in which $\Delta Vm1=2V$. The second linear impact object 24b experiences, as a result of the impact between the second linear impact object 24b and the first linear impact object 24a, a change of velocity $\Delta Vm2$ in which $\Delta Vm2 \approx 4V$. Thus, each impact in a plurality of temporally ordered impacts between a plurality of impact objects 24 produces a cumulatively increasing velocity acceleration.

Generally speaking, in a scenario in which there is an infinite mass ratio between adjacent impact objects 24, a succession of impacts between N impact objects 24 will produce an overall change in velocity $\Delta V$ of the lastly impacted impact object 24 in which $\Delta V=2^N V$, V being the common initial velocity V of the impact objects 24. This $\Delta V=2^N V$ change in velocity results if all of the impacts occur in the proper order, i.e., each impact occurring individually in a temporal order related to the spatial order 26 of the plurality of linear impact objects 24. Specifically, the correct temporal order is as follows: the first linear impact object 24a impacts the fixed-position object 64a, then the impacted first linear impact object 24a impacts the unimpacted second linear impact object 24b, then the impacted second linear impact object 24b impacts the unimpacted third linear impact object 24c, then the impacted third linear impact object 24c impacts the unimpacted fourth linear impact object 24d, etc.

For example, if there are one linear impact object 24 and the fixed position object 64a, the change in velocity has a value $\Delta V$ in which $\Delta V=2^1 V=2V$; if there are two linear impact objects 24 and the fixed position object 64a, the change in velocity has a value $\Delta V$ in which $\Delta V=2^2 V=4V$; if there are three linear impact objects 24 and the fixed-position object 64a, the change in velocity has a value $\Delta V$ in which $\Delta V=2^3 V=8V$; if there are four linear impact objects 24 and the fixed-position object 64a, the change in velocity has a value $\Delta V$ in which $\Delta V=2^4 V=16V$; etc.

The cumulative velocity acceleration which results from the plurality of temporally ordered impacts is also relevant to the impact involving the rotational impact object 25. In one embodiment, FIGS. 8a-c can be reinterpreted such that the second linear impact object is instead the rotational impact object 25 having initial linear velocity magnitude V in the direction depicted. The configuration of the shock apparatus 20 is such that the velocity amplification, and also the shock acceleration, experienced by the rotational impact object 25 can be selected to have a certain ratio of linear and rotational components. For example, in one embodiment, the shock acceleration can be selected to comprise only a rotational component. In another embodiment, the shock acceleration can be selected to comprise both a linear and rotational component. In one embodiment, the shock apparatus 20 and the rotational impact object 25 convert the purely linear shock acceleration that would be experienced by a linear impact object 24 into a mixture of linear and rotational shock acceleration, experienced by the rotational impact object 25 and thus also the text object 48, having a selectable proportion of linear and rotational components.

Embodiments of the shock apparatus 20 enable the plurality of impacts between the plurality of impact objects 22 to occur in the proper temporal order. A relatively high acceleration is thus enabled in part by the velocity amplification of the plurality of impacts. This provides one advantage of the present invention over other methods and apparatuses in that it enables a high acceleration in a relatively contained and safe apparatus. The plurality of impacts enabled by the present invention may be described, from one perspective, as spatially folded. That is, the shock apparatus 20 achieves an acceleration magnitude that would require the test object 48 be dropped from an impractically large height in a drop testing method or apparatus to achieve comparable acceleration magnitudes. The shock apparatus 20 of the present invention instead achieves the same result in a much smaller space, and thus could be considered to be spatially folded in comparison to the larger space required by drop testing. Similarly, to achieve comparable acceleration magnitudes by ballistic methods would be undesirably dangerous and expensive.

In one embodiment, the other object 64 does not have a fixed position, and instead is a variable position object. For example, the other object 64 can have a velocity in a direction moving towards the linear impact object 24.

In one embodiment of a method of using the shock apparatus 20, the plurality of impact objects 22 are provided with a predetermined initial velocity. For example, in one embodiment, the shock apparatus 20 is dropped from a height towards the other object 64. In such an embodiment, the plurality of impact objects 22 are provided with the predetermined initial velocity at least by the acceleration of gravity. In one embodiment, the plurality of impact objects 22 are only initially accelerated by gravity.

Figure 9:
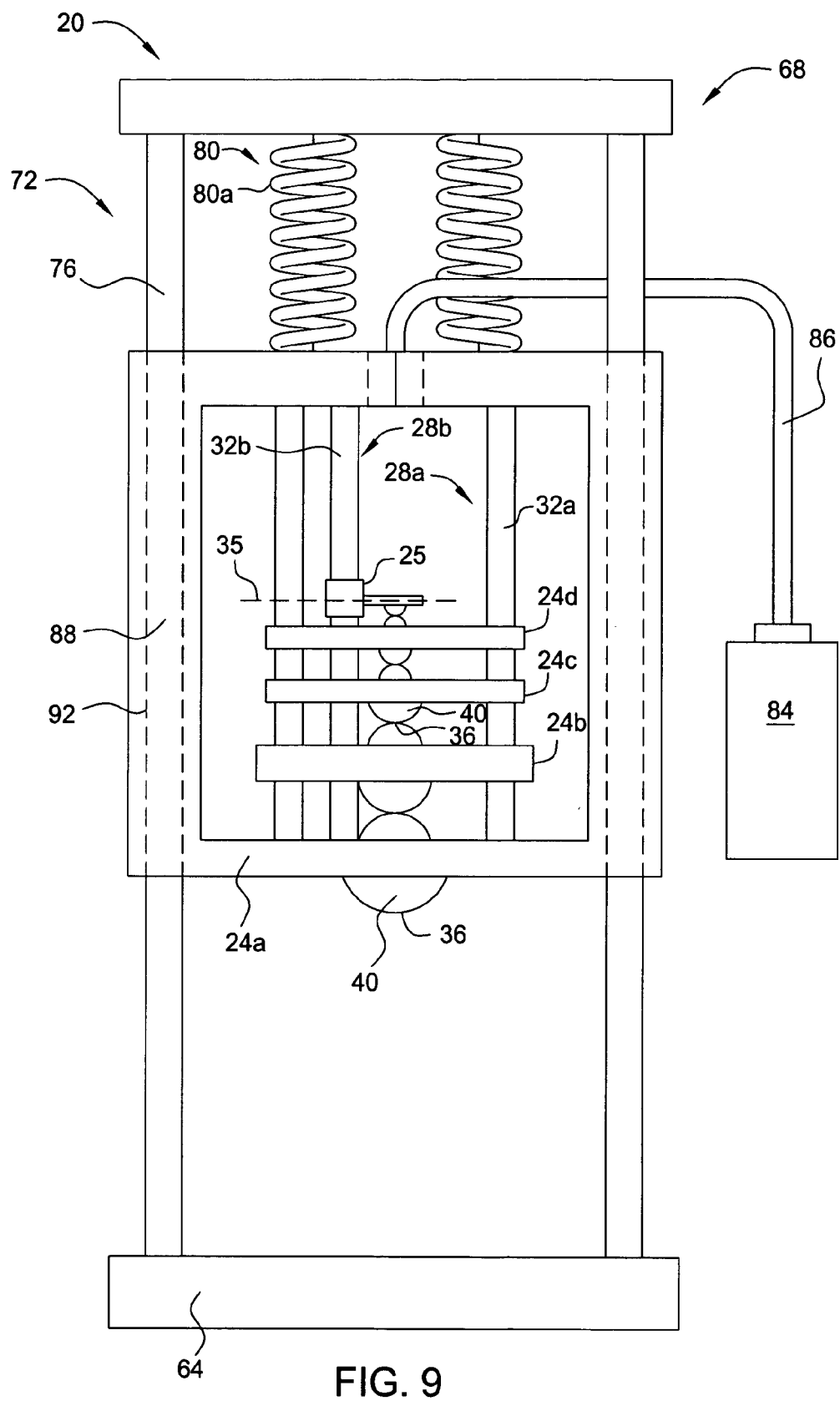
FIG. 9 depicts an embodiment of the shock apparatus comprising an embodiment of a launcher.

In one embodiment, the shock apparatus 20 comprises a launcher 68 which provides the predetermined initial velocity to the plurality of impact objects 22. The launcher 68 may comprise a variety of forms. FIG. 9 depicts one embodiment of the shock apparatus 20 comprising the launcher 68. The launcher 68 comprises a propelling means 80. For example, in the embodiment depicted, the propelling means 80 comprises a launcher spring 80a. The launcher spring 80a is compressed and calibrated to provide the predetermined initial velocity to the plurality of impact objects 22.

The launcher spring 80a is not the only possible propelling means, however. In another embodiment, the propelling means 80 comprises a ballistic means, such as, e.g., a canon. In one embodiment, the propelling means 80 comprises a gas source. For example, in one embodiment a pressurized gas source is focused about the plurality of impact objects 22 to provide the predetermined initial velocity. In one embodiment, the propelling means 80 comprises a magnetic propelling means having a magnet comprising at least one of: a permanent magnet, an electromagnet, or a superconducting magnet. The magnetic propelling means is arranged to provide a magnetic field about at least one of the plurality of impact objects 22.

In the embodiment depicted in FIG. 9, the launcher 68 comprises a launcher guide 72 to guide the movement of the plurality of impact objects 24 in the launcher 68. For example, in the embodiment depicted, the launcher guide 72 comprises at least one launcher guide rod 76. However, in other embodiments, other forms of the launcher guide 72 are possible. In one embodiment, the plurality of impact objects 22 or the guide 28 comprises an interface 88 to the launcher 68. For example, in the embodiment depicted in FIG. 9, the interface 88 comprises a surface 92 of the first linear impact object 24a which couples to the launcher guide 72.

In one embodiment, the propelling means 80 is external to the plurality of impact objects 22. For example, in some embodiments, any of the propelling means 80 discussed above can be external to the plurality of impact objects 22 and arranged to provide a force to at least one of the plurality of impact objects 22 to accelerate the plurality of impact objects 22 to the predetermined initial velocity.

In one embodiment, the propelling means 80 is internal to at least one of the plurality of impact objects 24. For example, in some embodiments, any of the propelling means 80 discussed above may be entirely or partially internal to at least one of the plurality of impact objects 22 and arranged to provide a force from the at least one of the plurality of impact objects 22 to the environment about the at least one of the plurality of impact objects 22 to accelerate the plurality of impact objects 22 to the predetermined initial velocity.

In one embodiment, the shock apparatus 20 comprises a camera 84 to record a visual record of the application of the shock acceleration provided to the test object 48. In one embodiment, the camera 84 is fixedly attached to at least one of the plurality of impact objects 22, and moves along with the at least one of the plurality of impact objects 22. In another embodiment, as depicted in FIG. 9, the camera 84 has a fixed position relative to the earth, and is attached to the at least one of the plurality of impact objects 22 by a flexible feed 86.

While the foregoing is directed to embodiments of the present invention, other and further embodiments of the invention may be devised without departing from the basic scope thereof, and the scope thereof is determined by the claims that follow. Various embodiments presented herein, or portions thereof, may be combined to create further embodiments. Furthermore, terms such as top, side, bottom, front, back, and the like are relative or positional terms and are used with respect to the exemplary embodiments illustrated in the figures, and as such these terms may be interchangeable.

The invention claimed is:

1. A shock apparatus, comprising:
   at least one linear impact object capable of movement along a first substantially linear path;
   a rotational impact object capable of rotation about an axis of rotation and movement along a second substantially linear path parallel to the first substantially linear path, a mass of the linear impact object being greater than an effective mass of the rotational impact object; and
   a guide to guide the movement of the linear and rotational impact objects along the first and second substantially linear parallel paths.

2. The shock apparatus of claim 1, wherein the linear impact object comprises an impact portion for impacting the rotational impact object, the impact portion having a selectable position, selecting the position determining the relative proportion of rotational and linear shock accelerations which an impact between the linear impact object and the rotational impact object provides to the rotational impact object.

3. The shock apparatus of claim 1, comprising a plurality of the linear impact objects spatially ordered according to decreasing mass along the first substantially linear path.

4. The shock apparatus of claim 2, comprising a plurality of spacers, one spacer between each adjacent pair of linear impact objects in the spatial order.

5. The shock apparatus of claim 2, wherein the guide and spacers enable a plurality of temporally ordered impacts involving the plurality of linear impact objects and the rotational impact object.

6. The shock apparatus of claim 1, wherein at least one of the linear impact object or the rotational impact object comprises an impact portion positioned at a point where the impact object impacts at least one other impact object; and
   wherein the properties of the impact portion are selectable to affect the magnitude and duration of a shock acceleration pulse experienced by the rotational impact object.

7. The shock apparatus of claim 2, wherein the properties of the impact portion which are selected include the hardness and elasticity of the impact portion.

8. The shock apparatus of claim 1, comprising a test object attached to the rotational impact object.

9. The shock apparatus of claim 1, wherein the guide comprises at least one first guide rod to guide the at least one linear impact object along the first substantially linear path, and at least one second guide rod to guide the rotational impact object along the second substantially linear path.

10. A method, comprising:
    providing at least one linear impact object capable of movement along a first substantially linear path and a rotational impact object capable of rotation about an axis of rotation and movement along a second substantially linear path, a mass of the linear impact object being greater than an effective mass of the rotational impact object;
    guiding the movement of the first impact object along the first substantially linear path and the second impact object along the second substantially linear path; and
    impacting the linear impact object and the rotational impact object in a plurality of temporally ordered impacts.

11. The method of claim 10, comprising:
    providing an impact portion of the linear impact object for impacting the rotational impact object, the impact portion having a selectable position; and
    selecting the position of the impact portion to determine the relative proportion of rotational and linear shock acceleration which an impact between the linear impact object and the rotational impact object provides to the rotational impact object.

12. The method of claim 10, wherein the providing at least one linear impact object comprises providing a plurality of the linear impact objects spatially ordered according to decreasing mass along the first substantially linear path.

13. The method of claim 12, comprising:
    providing a plurality of spacers, one spacer between each adjacent pair of linear impact objects in the spatial order.

14. The method of claim 10, comprising:
    positioning an impact portion of at least one of the linear impact object or the rotational impact object at a point where the impact object impacts at least one other impact object; and
    selecting the properties of the impact portion to affect the magnitude and duration of a shock acceleration pulse experienced by the rotational impact object.

15. The method of claim 14, wherein the selecting the properties of the impact portion comprises selecting the hardness and elasticity of the impact portion.

16. The method of claim 10, comprising:
    attaching a test object to the rotational impact object.

17. The method of claim 10, comprising:
    providing at least one first guide rod to guide the at least one linear impact object along the first substantially linear path, and at least one second guide rod to guide the rotational impact object along the second substantially linear path.

18. A shock apparatus, comprising:
    first impacting means for providing at least one linear velocity changing impact involving a linear impact object, the at least one linear velocity-changing impact resulting in an impacted linear impact object having a resulting linear velocity which is changed relative to an initial linear velocity of the linear impact object;

second impacting means for providing a rotational velocity changing impact between the impacted linear impact object and a rotational impact object, the rotational velocity changing impact resulting in an impacted rotational impact object having a rotational velocity different than an initial rotational velocity of the rotational impact object.

19. The shock apparatus of claim 18, comprising a rotational velocity selection means for selecting the rotational velocity provided by the rotational velocity changing impact.

20. The shock apparatus of claim 19, wherein the rotational velocity selection means comprises an impact portion having selectable properties, the impact portion being of at least one of: the first impact object or the second impact object.

21. The shock apparatus of claim 20, wherein the selectable properties include at least one of: a first material of a first impact portion of the first impact object, a second material of a second impact portion of the second impact object, a structure of the first impact portion of the first impact object, or a structure of the second impact portion of the second impact object.

* * * * *